United States Patent
Ono et al.

(10) Patent No.: US 7,006,926 B2
(45) Date of Patent: Feb. 28, 2006

(54) CARBON DIOXIDE SENSOR

(75) Inventors: Shizuko Ono, Tokyo (JP); Akira Shibue, Tokyo (JP); Noboru Yamazoe, Kasuga (JP); Kengo Shimanoe, Onojyo (JP); Kenji Obata, Onojyo (JP); Norio Miura, Fukuoka (JP)

(73) Assignee: TDK Corporation, Tokyo (JP)

( * ) Notice: Subject to any disclaimer, the term of this patent is extended or adjusted under 35 U.S.C. 154(b) by 21 days.

(21) Appl. No.: 10/359,696

(22) Filed: Feb. 7, 2003

(65) Prior Publication Data

US 2004/0158410 A1 Aug. 12, 2004

(51) Int. Cl.
*G01N 19/00* (2006.01)
(52) U.S. Cl. ......................... 702/24; 204/424
(58) Field of Classification Search ............. 702/24; 204/426, 424; 205/784, 782.5, 787; 528/405
See application file for complete search history.

(56) References Cited

U.S. PATENT DOCUMENTS 5,378,274 A * 1/1995 Yokoyama et al. ......... 106/410
6,325,905 B1 * 12/2001 Matsui et al. ............... 204/424

FOREIGN PATENT DOCUMENTS

| JP | B2-7-85071 | 9/1995 |
|---|---|---|
| JP | B2-2598172 | 1/1997 |
| JP | B2-2974088 | 9/1999 |
| JP | B2-2974090 | 9/1999 |
| JP | 411271270 A | * 10/1999 |
| JP | A-11-271270 | 10/1999 |
| JP | 2000048836 A | * 2/2000 |
| JP | A-2000-65790 | 3/2000 |
| JP | A-2000-88797 | 3/2000 |
| JP | A-2000-88798 | 3/2000 |
| JP | A-2000-88799 | 3/2000 |
| JP | A-2001-281205 | 10/2001 |
| JP | 2002107332 | * 4/2002 |
| JP | A-2002-107326 | 4/2002 |
| JP | A-2002-107327 | 4/2002 |
| JP | A-2002-107328 | 4/2002 |
| JP | A-2002-107329 | 4/2002 |
| JP | A-2002-107330 | 4/2002 |
| JP | A-2002-107331 | 4/2002 |
| JP | A-2002-107332 | 4/2002 |

(Continued)

OTHER PUBLICATIONS

Roles of Humidity in NASICON-Based $CO_2$ Sensor Operative at Room Temperature, The 9th International Meeting on Chemical Sensors held in the Boston Park Plaza, Massachusetts, USA on Jul. 7-10, 2002.

(Continued)

*Primary Examiner*—Michael Nghiem
*Assistant Examiner*—Xiuqin Sun
(74) *Attorney, Agent, or Firm*—Oliff & Berridge, PLC

(57) ABSTRACT

A carbon oxide sensor having high sensitivity capable of reduction of influence of humidity is provided. A detection electrode and a counter electrode are provided on one side of an electrolyte, respectively. The detection electrode contains a metal oxide and a metal carbonate including plural components. The metal carbonate preferably contains a first component of alkali metal carbonate and a second component of at least one element selected from the group consisting of alkali earth metal carbonate, transition metal carbonate, zinc carbonate, cadmium carbonate, indium carbonate, lead carbonate and bismuth carbonate. Specifically, it is preferable to contain the first component including $Li_2CO_3$ and the second component including at least one element selected from the group consisting of $BaCO_3$, $CaCO_3$ and $SrCO_3$.

3 Claims, 6 Drawing Sheets

FOREIGN PATENT DOCUMENTS

| | | | |
|---|---|---|---|
| JP | A-2002-107337 | | 4/2002 |
| JP | 2002365260 | * | 12/2002 |

OTHER PUBLICATIONS

Influences of Water Vapor on NASICON-Based $CO_2$ Sensor Operative at Room Temperature, The 9th International Meeting on Chemical Sensors held in the Boston Park Plaza, Massachusetts, USA on Jul. 7-10, 2002.

Proceedings of the 5th East Asion Conference on Chemical Sensors, The 33rd Chemical Sensor Symposium, Dec. 4-7, 2001, Huis Ten Bosch, Sasebo-shi, Nagasaki, Japan,; pp. 129-131.

* cited by examiner

CARBON DIOXIDE SENSOR

BACKGROUND OF THE INVENTION

1. Field of the Invention

The present invention relates to a carbon dioxide sensor used for an indoor and outdoor environmental monitoring and control, an agro-industrial process such as greenhouse horticulture, disaster prevention, a measurement of metabolic function of body surface, and a medical care.

2. Description of the Related Art

In recent years, a need for carbon dioxide sensor is increasing particularly in detection of dirty air in the room caused by the spread of air conditioner, detection of contamination air in livestock facilities, control of the growth of plants in greenhouse and various industrial processes, and various kinds of carbon dioxide sensors have been reported.

Specifically, an infrared absorption carbon dioxide sensor has been in practical use, for example. However, this carbon dioxide sensor is not widely used because of the size and the cost of the apparatus. In addition, a carbon dioxide sensor using a semiconductor has been also in practical use; however, it is difficult to monitor only the carbon dioxide concentration due to poor carbon dioxide selectivity.

On the other hand, a carbon dioxide sensor using a solid electrolyte has been proposed as a compact and inexpensive sensor. An example of such carbon dioxide sensor is so-called an electromotive force detection sensor obtained by forming a pair of electrodes on a solid electrolyte having an alkali metal ion conductivity such as NASICON (sodium super ion conductor: $Na_3Zr_2Si_2PO_{12}$). One electrode is used as a detection electrode with a metal carbonate layer such as sodium carbonate which forms a dissociation equilibrium with carbon dioxide. The other electrode is used as a carbon dioxide non-sensitive electrode (refer to Maruyama et al. "Solid State Ionics", Vol 23, No. 1/2, p.107–112 (1987)).

According to this carbon dioxide sensor, an excellent carbon dioxide sensing property can be achieved. However, there has been a problem that this carbon dioxide sensor is susceptible to humidity, because the metal carbonate is used as the detection electrode. Therefore, a carbon dioxide sensor that is lightly affected by humidity by utilizing the mixture of alkali metal carbonate and alkali earth metal carbonate, or solid solution for the detection electrode has been proposed (refer to Publication of Examined Application No. Hei 7-85071, Japanese Patent No. 2598172, Japanese Patent No. 2974088 and Japanese Patent No. 2974090, for example).

The operation temperature of the carbon dioxide sensor is as high as 400° C. to 700° C., so the overall power consumption of the sensor is high and there has been a problem that the heat deterioration of materials occur. Further, heat of a few hundreds of temperature raises temperature around the sensor even from a small heater and generates convection of the air. This affects subtly on the environment for monitoring, which is a problem.

Accordingly, a carbon dioxide sensor using a tin oxide ($SnO_2$) semiconductor containing stibium (Sb) or vanadium (V) as the detection electrode has been proposed (refer to S. Breikhin et al. "Applied Physics", A57, 37–43 (1993), for example). Another carbon dioxide sensor in which the detection electrode is formed of a metal oxide layer, or a metal oxide layer dispersed metal carbonate or hydrogen carbonate has been proposed (refer to Japanese Patent Laid-Open No. Hei 11-271270 or Japanese Patent Laid-Open No. 2000-88799). These carbon dioxide sensors are operatable at room temperature.

However, the carbon dioxide sensor using the tin oxide semiconductor as the detection electrode requires four or more minutes for response and the difficulty of prompt measurement has been a problem. In addition, there has been another problem that the response time or sensitivity varies by humidity because water vapor is involved in the detection mechanism in this carbon dioxide sensor. Also, the carbon dioxide sensor using the metal oxide is susceptible to humidity. Although the influence of humidity on the sensitivity is small, the absolute value of the electromotive force output varies and the correction is required according to humidity, which is a problem.

SUMMARY OF THE INVENTION

The present invention has been achieved in view of the above problems. It is an object of the invention to provide a carbon dioxide sensor which is operatable at room temperature and reduce the influence of humidity.

A first carbon dioxide sensor of the invention is provided with a detection electrode and a counter electrode on an electrolyte, and the detection electrode comprises a metal oxide layer including a metal oxide and a metal carbonate layer including metal carbonate placed between the metal oxide layer and the electrolyte.

In the first carbon dioxide sensor of the invention, the metal oxide layer and the metal carbonate layer are laminated, so it is operative at room temperature and has less influence of humidity.

Preferably, the metal carbonate layer includes lithium carbonate and is formed at a temperature lower than a melting point of containing metal carbonate.

The metal oxide layer preferably comprises at least one element selected from the group consisting of tin oxide, indium oxide, cobalt oxide, tungsitc oxide, zinc oxide, lead oxide, copper oxide, iron oxide, nickel oxide, chromium oxide, cadmium oxide, bismuth oxide, manganese oxide, yttrium oxide, antimony oxide, lanthanum oxide, cerium oxide, praseodymium oxide, neodymium oxide, silver oxide, lithium oxide, sodium oxide, potassium oxide, rubidium oxide, magnesium oxide, calcium oxide, strontium oxide and barium oxide, and specifically, contains the composite oxide including tin and indium. The electrolyte includes a metal ion conductor, preferably.

A second carbon dioxide sensor of the invention is provided with a detection electrode and a counter electrode on an electrolyte, and the detection electrode comprises a metal oxide and a metal carbonate including plural components.

In the second carbon dioxide sensor of the invention, the detection electrode comprises the metal oxide and the metal carbonate including plural components, so it is operative at room temperature and has less influence of humidity. Incidentally, the "metal carbonate including plural components" includes the cases where the plural kinds of metal carbonates are mixed without mutual chemical bonding, forms the complex carbonate with mutual chemical bonding, or both in the specification.

The metal carbonate comprises a first component of alkali metal carbonate and a second component of at least one element selected from the group consisting of alkali earth metal carbonate, transition metal carbonate, zinc carbonate, cadmium carbonate, indium carbonate, lead carbonate and bismuth carbonate, preferably. The first component includes lithium carbonate and the second component includes at least one element selected from the group consisting of barium carbonate, calcium carbonate and strontium carbonate, preferably.

The detection electrode preferably comprises a metal oxide layer including metal oxide and a metal carbonate layer including metal carbonate placed between the metal oxide layer and the electrolyte. In this case, the metal carbonate layer is formed at a temperature lower than a melting point of containing metal carbonate, preferably.

The metal oxide layer preferably comprises at least one element selected from the group consisting of tin oxide, indium oxide, cobalt oxide, tungsitc oxide, zinc oxide, lead oxide, copper oxide, iron oxide, nickel oxide, chromium oxide, cadmium oxide, bismuth oxide, manganese oxide, yttrium oxide, antimony oxide, lanthanum oxide, cerium oxide, praseodymium oxide, neodymium oxide, silver oxide, lithium oxide, sodium oxide, potassium oxide, rubidium oxide, magnesium oxide, calcium oxide, strontium oxide and barium oxide, and specifically it is preferable to contain the composite oxide including tin and indium.

The electrolyte preferably includes a metal ion conductor. The detection electrode and counter electrode are provided on the same side of the electrolyte.

DETAILED DESCRIPTION OF THE PREFERRED EMBODIMENTS

Embodiments of the present invention will be described in detail below with reference to accompanying drawings.

[First Embodiment]

Figure 1:
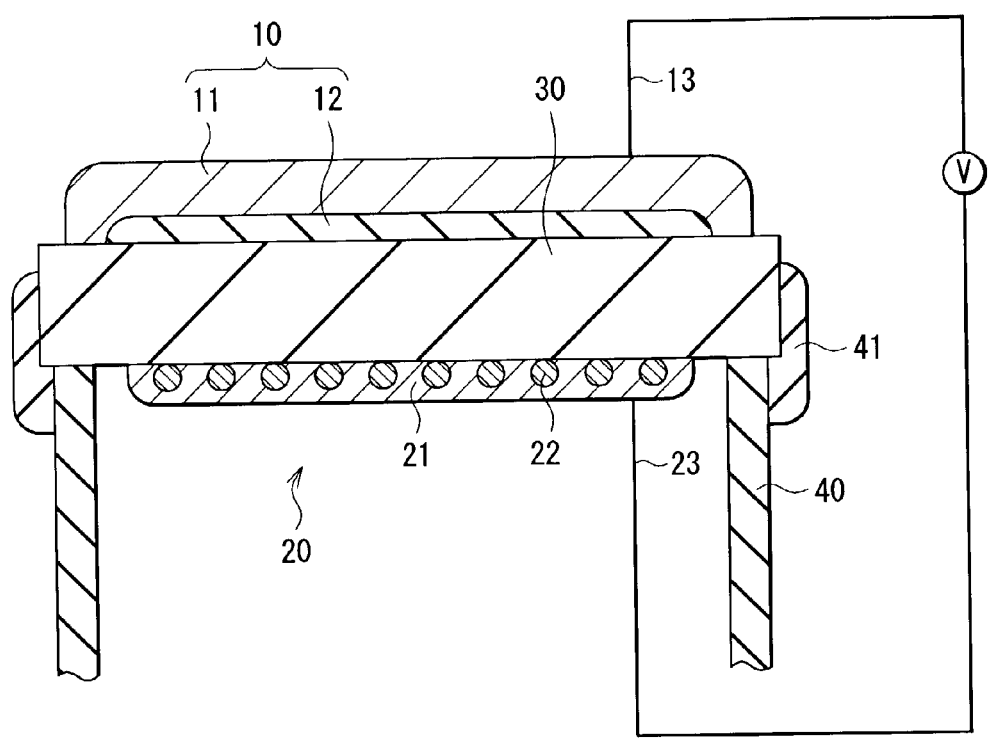
FIG. 1 is a sectional view showing a configuration of a carbon dioxide sensor according to a first embodiment of the invention.

FIG. 1 shows a configuration of a carbon dioxide sensor according to a first embodiment of the invention. In the carbon dioxide sensor, a detection electrode 10 is placed on the opposite side of a counter electrode 20 sandwiching an electrolyte 30 in between. The detection electrode 10 and counter electrode 20 are connected to a potentiometer by leads 13 and 23. A quartz glass tube 40 is attached with an adhesive layer 41 on the electrolyte 30 for preventing the counter electrode 20 to be exposed in the measurement atmosphere.

The detection electrode 10 comprises a metal oxide layer 11 including metal oxide and a metal carbonate layer 12 including metal carbonate. The metal carbonate layer 12 is placed between the metal oxide layer 11 and the electrolyte 30. With such a layer structure, the influence of humidity can be decreased and the carbon dioxide sensing property can be improved. Preferably, the thicknesses of the metal oxide layer 11 and the metal carbonate layer 12 are 10 nm to 500 $\mu$m, for example, because higher effects can be achieved. The metal carbonate in the specification means the so-called normal salt which does not contain acid salt, that is, hydrogen carbonate and basic salt.

Preferably, the metal oxide layer 11 includes at least one element selected from the group consisting of tin oxide ($SnO$, $SnO_2$), indium oxide ($In_2O_3$), cobalt oxide ($Co_3O_4$), tungsitc oxide ($WO_3$), zinc oxide ($ZnO$), lead oxide ($PbO$), copper oxide ($CuO$), iron oxide ($Fe_2O_3$, $FeO$), nickel oxide ($NiO$), chromium oxide ($Cr_2O_3$), cadmium oxide ($CdO$), bismuth oxide ($Bi_2O_3$), manganese oxide ($MnO_2$, $Mn_2O_3$), yttrium oxide ($Y_2O_3$), antimony oxide ($Sb_2O_3$), lanthanum oxide ($La_2O_3$), cerium oxide ($CeO_2$), praseodymium oxide ($Pr_6O_{11}$), neodymium oxide ($Nd_2O_3$), silver oxide ($Ag_2O$), lithium oxide ($Li_2O$), sodium oxide ($Na_2O$), potassium oxide ($K_2O$), rubidium oxide ($Rb_2O$), magnesium oxide ($MgO$), calcium oxide ($CaO$), strontium oxide ($SrO$) and barium oxide ($BaO$), for example.

Using these metal oxides allows prompt measurement at a low temperature. These metal oxides may be slightly deviated from the stoichiometric composition. When including two or more oxides, a composite oxide or a mixture of these oxides may be included.

As the metal oxide, it is preferable to include at least one element selected from the group consisting of tin oxide, indium oxide, cobalt oxide, tungsitc oxide, zinc oxide, lead oxide, copper oxide, iron oxide, nickel oxide, chromium oxide, cadmium oxide and bismuth oxide, and further at least one element selected from the group consisting of tin oxide, indium oxide, lead oxide and tungsitc oxide because the higher effects can be achieved. Also, when the composite oxide including tin and indium is contained, the high conductivity is achieved, which is preferable.

The metal carbonate layer 12 preferably includes at least one element selected from the group consisting of lithium carbonate ($Li_2CO_3$), sodium carbonate ($Na_2CO_3$), potassium carbonate ($K_2CO_3$), rubidium carbonate ($Rb_2CO_3$), cesium carbonate ($Cs_2CO_3$), magnesium carbonate ($MgCO_3$), calcium carbonate ($CaCO_3$), strontium carbonate ($SrCO_3$), barium carbonate ($BaCO_3$), manganese carbonate ($Mn(CO_3)_2$, $Mn_2(CO_3)_3$), iron carbonate ($Fe_2(CO_3)_3$, $FeCO_3$), nickel carbonate ($NiCO_3$), copper carbonate ($CuCO_3$), cobalt carbonate ($Co_2(CO_3)_3$), chromium carbonate ($Cr_2(CO_3)_3$), zinc carbonate ($ZnCO_3$), silver carbonate ($Ag_2CO_3$), cadmium carbonate ($CdCO_3$), indium carbonate ($In_2(CO_3)_3$), yttrium carbonate ($Y_2(CO_3)_3$), lead carbonate ($PbCO_3$), bismuth carbonate ($Bi_2(CO_3)_3$), lanthanum carbonate ($La_2(CO_3)_3$), cerium carbonate ($Ce(CO_3)_3$), praseodymium carbonate ($Pr_6(CO_3)O_{11}$) and neodymium carbonate ($Nd_2(CO_3)_3$), for example.

Using these metal carbonates allows the improvement of carbon dioxide sensing property. These metal carbonates may be slightly deviated from the stoichiometric composition. When including two or more metal carbonates, a compound or a mixture of these carbonates may be included. As the metal carbonate, it is preferable to include alkali metal carbonate, specifically, lithium carbonate because it can reduce the influence of humidity.

The metal carbonate layer 12 may further include metal hydrogen carbonate. This is because the metal hydrogen carbonate may be generated during the measurement of carbon dioxide.

Although a method of forming the metal oxide layer 11 and the metal carbonate layer 12 is not limited, a method that a powder paste of the metal carbonate is applied to the electrolyte 30 and heat-treated to form the metal carbonate layer 12, and then a metal oxide paste is applied thereon and heat-treated to form the metal oxide layer 11 is preferable.

In addition, the metal carbonate layer 12 and the metal oxide layer 11 are preferably formed by a method that after applying the powder paste of the metal carbonate to the electrolyte 30, the metal oxide is applied thereon and heat-treated at a temperature lower than a melting point of containing metal carbonate. If the metal carbonate layer 12 and the metal oxide layer 11 are heated at a temperature higher than the melting point of the metal carbonate, the metal carbonate reacts with the metal oxide or the electrolyte 30 and produce reactant and it is easily affected by humidity.

The preferable average grain size of the used metal oxide and the metal carbonated is 10 nm to 100 $\mu$m. A solvent not reacting with the metal oxide and the metal carbonate and having a relatively low room steam pressure and good workability is used as the solvent of the paste. In particular, $\alpha$-terpineol, ethylene glycol, glycerin or the like is preferable. The slurry viscosity is 0.01 Pa·s to 10,000 Pa·s, preferably.

The detection electrode 10 may have collector (not shown) on the top surface or in the metal oxide layer 11. It is effective when the conductivity of the metal oxide layer 11 is not so high. However, when using the composite oxide including indium and tin, high conductivity can be achieved, so no collector is required. The collector is formed of metal, preferably, any one or more elements of gold (Au), platinum (Pt), silver (Ag), rubidium (Rb), rhodium (Rh), palladium (Pd), iridium (Ir), nickel (Ni), copper (Cu) and chromium (Cr). The collector is preferably formed of a porous metal to diffuse carbon dioxide. The porous metal is preferably a metal mesh or a powder electrode which is formed by pressure bonding or screen printing a metal powder paste. In particular, a powder electrode is preferable.

The screen printing is a method of applying a metal powder paste to a substrate through mesh screen and in this case a porous electrode in which metal particles are interconnected is formed. The average grain size of the used metal powder is 10 nm to 100 $\mu$m and preferably 10 nm to 10 $\mu$m for good printing. A solvent not reacting with the used metal and having a relatively low room steam pressure and good workability is used as the solvent of the paste. In particular, $\alpha$-terpineol, ethylene glycol, glycerin or the like is preferable. The slurry viscosity is 0.01 Pa$\mu$s to 10,000 Pa·s, preferably.

The porous metal formed by sputtering also can be used as collector. Argon (Ar), helium (He), oxygen ($O_2$), nitrogen ($N_2$) and the like are preferably used as a sputtering gas and the preferable pressure during the deposition is within the range of 0.013 Pa to 66.7 Pa. The surface of the electrode can be porous by resistance heating deposition.

The counter electrode 20 has a thickness of 0.1 $\mu$m to 100 $\mu$m, for example and formed of metal or metal oxide. Preferably, any one or more metals constituting the collector (not shown) of the detection electrode 10 or oxides of those metals, or the metal oxides constituting the metal oxide layer 11 is used for forming the counter electrode 20, for example. Specifically, in the counter electrode 20 formed of the metal oxide, the influence of concurrent gas is reduced, higher carbon dioxide selectivity can be achieved, humidity resistance is improved, and the influence of humidity during the measurement under a low temperature is reduced in particular.

The counter electrode 20 is preferably formed of the porous metal or the porous metal oxide like the collector of the detection electrode 10. Specifically, the powder electrode which is formed by pressure bonding or screen printing of the metal oxide powder paste is preferable. The carbon dioxide sensor comprises a powder electrode 21 and a gold mesh 22. The metal powder or the metal oxide powder for forming the powder electrode 21 preferably has an average grain size of 10 nm to 100 $\mu$m, and more preferably 0.5 $\mu$m to 100 $\mu$m. A solvent not reacting with the used metals or metal oxides and having a relatively low room steam pressure and good workability is preferably used as the solvent of the paste. In particular, $\alpha$-terpineol, ethylene glycol, glycerin or the like is preferable. The slurry viscosity is 0.01 Pa·s to 10,000 Pa·s, preferably.

The electrolyte 30 has a thickness of 1 $\mu$m to 5 mm, for example and preferably include a metal ion conductor. Examples of the metal ion conductor are Na—$\beta$" alumina, Na—$\beta$ alumina, $Na_3Zr_2PSi_2O_{12}$, $Na_3Zr_2Si_2PO_{12}$ (NASICON), Na—$\beta Ga_2O_3$, Na—$Fe_2O_3$, $Na_3Zr_2PSi_2P_2O_{12}$, Li—$\beta$ alumina, $Li_{1.4}Zn(GeO_4)_4$, $Li_3Zn_{0.5}GeO_4$, $Li_{3.5}Zn_{0.25}GeO_4$ (LISICON), lithium ion exchange NASICON, $Li_5AlO_4$, $Li_{1.4}Ti_{1.6}In_{0.4}P_3O_{12}$, K—$\beta$ alumina, $K_{1.6}Al_{0.8}Ti_{7.2}O_{16}$, $K_2MgTi_7O_{16}$, CaS or the like. Of these metal ion conductors, sodium ion conductor or lithium ion conductor is preferable and NASION, LISICON, lithium ion exchange NASICON or the like is more preferable because the ion conduction required for the response of the sensor at a low temperature is confirmed. These metal ion conductors may be slightly deviated from the stoichiometric composition. Polyelectrolyte can be used as well.

The electrolyte 30 may contain aluminum oxide ($Al_2O_3$), silicon oxide ($SiO_2$), zirconium oxide ($ZeO_2$), silicon carbide (SiC), silicon nitride ($Si_3N_4$), iron oxide ($Fe2O_3$) or the like with 50% by mass or less in addition to the metal ion conductor as a reinforcer not to prevent the ion conductivity. These elements may be slightly deviated from the stoichiometric composition.

In order to form the electrolyte 30, any generally used solid-phase method, sol-gel method, coprecipitation method and the like can be used, and preferably sol-gel method is used.

In the carbon dioxide sensor, when the detection electrode 10 is exposed to the measurement atmosphere, carbon dioxide in the measurement atmosphere diffuses into the metal oxide layer 11 and reaches the metal carbonate layer 12. The dissociation equilibrium in the metal carbonate and carbon dioxide changes in the metal carbonate layer 12 and the metal ion activity in the electrolyte 30 near the detection electrode 10 also changes. Thereby, the electromotive force is generated between the detection electrode 10 and the counter electrode 20 and carbon dioxide concentration is measured.

In particular, the carbon dioxide sensor has the layer structure of the metal oxide layer 11 and the metal carbonate layer 12 and therefore, it is not susceptible to humidity and a stable measurement results are achieved at room temperature at 30% or more humidity. The carbon dioxide sensing property is also improved. When lithium carbonate is included in the metal carbonate layer 12, or the metal carbonate layer 12 is formed at a temperature lower than the melting point of containing metal carbonate, more stable results can be achieved.

According to the embodiment, the carbon dioxide sensor comprises the metal carbonate layer 12 and the metal oxide layer 11 on the electrolyte 30 in this order, so it is operatable at room temperature and has less influence of humidity, and the carbon dioxide sensing property is improved. As a result, the carbon dioxide concentration can be detected easily with high accuracy.

Specifically, when lithium carbonate is included in the metal carbonate layer 12 or the carbonate layer 12 is formed at a temperature lower than the melting point of containing metal carbonate, the influence of humidity can be decreased and the carbon dioxide sensing property is improved.

[Second Embodiment]

Figure 2:
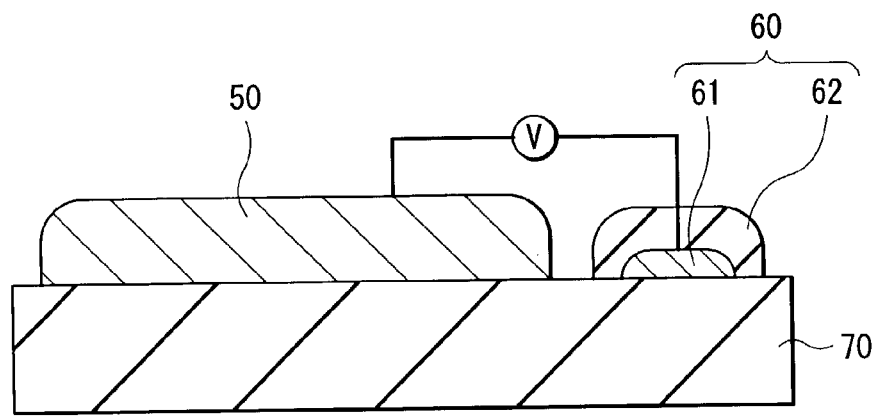
FIG. 2 is a sectional view showing a configuration of a carbon dioxide sensor according to a second embodiment of the invention.

FIG. 2 shows the configuration of a carbon dioxide sensor according to a second embodiment of the invention. In the carbon dioxide sensor, a detection electrode 50 and a counter electrode 60 are placed on the same side of an electrolyte 70. The detection electrode 50 and a counter electrode 60 are connected to a potentiometer by leads. The detection electrode 50 may be placed on the opposite side of the counter electrode 60 sandwiching the electrolyte 70 in between, as shown in FIG. 1; however, with this configuration, that is, the detection electrode 50 and the counter electrode 60 are placed on the same surface of the electrolyte 70, it facilitate the extraction of the leads and the manufacturing process. In addition, the miniaturization of device can be improved, which is preferable.

The detection electrode 50 has a thickness of, for example 0.1 $\mu$m to 100 $\mu$m and contains the metal oxide and the metal carbonate including plural components. The metal oxide and the metal carbonate are dispersed with each other.

The same metal oxides constituting the detection electrode 10 in the first embodiment can be used, for example.

The metal carbonate contains a first component consisting of at least one element of alkali metal carbonate and a second component consisting of at least one element of alkali earth metal carbonate and transition metal carbonate, for example. The influence of humidity is reduced with such a mixture. Alkali metal carbonate, alkali earth metal carbonate and transition metal carbonate may be mixed without mutual chemical bonding, mixed with mutual chemical bonding to form the complex carbonate, or some of them form the complex carbonate and some of them are mixed. Each of alkali metal carbonate, alkali earth metal carbonate and transition metal carbonate may be mixed, bonded or both when including plural kinds of components.

Alkali metal carbonate includes lithium carbonate ($Li_2CO_3$), sodium carbonate ($Na_2CO_3$), potassium carbonate ($K_2CO_3$), rubidium carbonate ($Rb_2CO_3$), or cesium carbonate ($Cs_2CO_3$), for example. Alkali earth metal carbonate includes magnesium carbonate ($MgCO_3$), calcium carbonate ($CaCO_3$), strontium carbonate ($SrCO_3$), or barium carbonate ($BaCO_3$), for example.

Transition metal carbonate is elements belong to Group III to Group XI of long period periodic table. Examples of transition metal carbonate are manganese carbonate ($Mn(CO_3)_2$, $Mn_2(CO_3)_3$), iron carbonate ($Fe_2(CO_3)_3$, $FeCO_3$), nickel carbonate ($NiCO_3$), copper carbonate ($CuCO_3$), cobalt carbonate ($Co_2(CO_3)_3$), chromium carbonate ($Cr_2(CO_3)_3$), silver carbonate ($Ag_2CO_3$), yttrium carbonate ($Y_2(CO_3)_3$), lanthanum carbonate ($La_2(CO_3)_3$), cerium carbonate ($Ce(CO_3)_3$), praseodymium carbonate ($Pr_6(CO_3)O_{11}$) and neodymium carbonate ($Nd_2(CO_3)_3$). These metal carbonates may be slightly deviated from the stoichiometric composition.

Preferably the first component includes at least lithium carbonate and the second component includes at least one element selected from the group consisting of barium carbonate, calcium carbonate and strontium carbonate because higher effects can be achieved. Specifically, it is preferable to include lithium carbonate in concurrent with at least one element selected from the group consisting of barium carbonate, calcium carbonate and strontium carbonate.

The second component may be include at least one element selected from the group consisting of zinc carbonate ($ZnCO_3$), cadmium carbonate ($CdCO_3$), indium carbonate ($In_2(CO_3)_3$), lead carbonate ($PbCO_3$) and bismuth carbonate ($Bi_2(CO_3)_3$). With these elements, the influence of humidity is reduced similarly. These elements may be included together with the elements of alkali earth metal carbonate or transition metal carbonate and be substituted for these elements. When including two or more kinds of these elements, these elements and others may be mixed, bonded or both as described above.

The detection electrode 50 may contain metal hydrogen carbonate, because the metal hydrogen carbonate may be generated during the measurement of carbon dioxide.

Although a method of forming the detection electrode 50 is not limited, a method that a paste including the metal oxide powder and the metal carbonate powder is applied to the electrolyte 70 and heat-treated at a temperature lower than a melting point of containing metal carbonate, as described in the first embodiment, for example. If the metal oxide and the metal carbonate are heat-treated at a temperature higher than the melting point of the metal carbonate, the metal carbonate reacts with the metal oxide or the electrolyte 70 and produce reactant and it becomes susceptible to humidity.

The average grain size of the used metal oxide and the metal carbonate, the solvent of the paste or the like are the same as described in the first embodiment.

The detection electrode 50 may comprise the collector on the top surface thereof or therein like the first embodiment. The structure of the collector is the same as the first embodiment.

The counter electrode 60 has a thickness of, for example about 0.1 $\mu$m to 100 $\mu$m and comprises a standard layer 61 provided on the electrolyte 70 and a protective layer 62 provided to cover the standard layer 61.

The standard layer 61 is formed of metal or metal oxide, for example. The metal or the metal oxide of the standard layer 61 is preferably any one or more elements of the metal oxides of the detection electrode 10 in the first embodiment, the metal of the collector of the detection electrode 10 or the oxides thereof, for example. When using the metal oxide for forming the standard layer 61, the influence of concurrent gas is reduced, the high carbon dioxide selectivity is achieved, the humidity resistance is improved, and the influence of humidity during the measurement under a low temperature is reduced in particular.

The standard layer 61 is preferably formed of the porous metal or the porous metal oxide and the powder electrode formed by pressure bonding or screen printing of the metal oxide powder paste is more preferable. The details of the powder electrode are as described in the counter electrode 20 in the first embodiment.

The protective layer 62 is provided for reducing the influence of humidity by preventing the standard layer 61 from exposing to the measurement atmosphere and formed of fluororesin, inorganic ceramics, cobaltate or the like, preferably. The protective layer 62 is dispensable; however it is preferable to provide to reduce the influence of humidity.

The electrolyte 70 is the same as the electrolyte 30 of the first embodiment.

In the carbon dioxide sensor, when the detection electrode 50 is exposed in the measurement atmosphere, carbon dioxide in the measurement atmosphere diffuses into the detection electrode 50 and the dissociation equilibrium of the metal carbonate with carbon dioxide changes. Accordingly, the metal ion activity in the electrolyte 70 near the detection electrode 50 changes. As a result, the electromotive force is generated between the detection electrode 50 and the counter electrode 60 and carbon dioxide concentration is measured.

The carbon dioxide sensor contains the metal oxide and the metal carbonate including plural components, so it is operative at room temperature and is not susceptible to humidity and the stable measurement results are achieved at room temperature at 30% or more of humidity. When including the first component of alkali metal carbonate and the second component of at least one element selected from the group consisting of alkali earth metal carbonate and transition metal carbonate, more stable results can be achieved.

According to the embodiment, the detection electrode 50 contains the metal carbonate including plural components, so it is operative at room temperature and has less influence of humidity. As a result, the carbon dioxide concentration can be detected easily with high accuracy.

Specifically, when including the first component of alkali metal carbonate and the second component of at least one element selected from the group consisting of alkali earth metal carbonate, transition metal carbonate, zinc carbonate, cadmium carbonate, indium carbonate, lead carbonate and bismuth carbonate, and further including lithium carbonate in the first component and including at least one element selected from the group consisting of barium carbonate, potassium carbonate and strontium carbonate in the second component, the influence of humidity can be reduced more.

[Third Embodiment]

Figure 3:
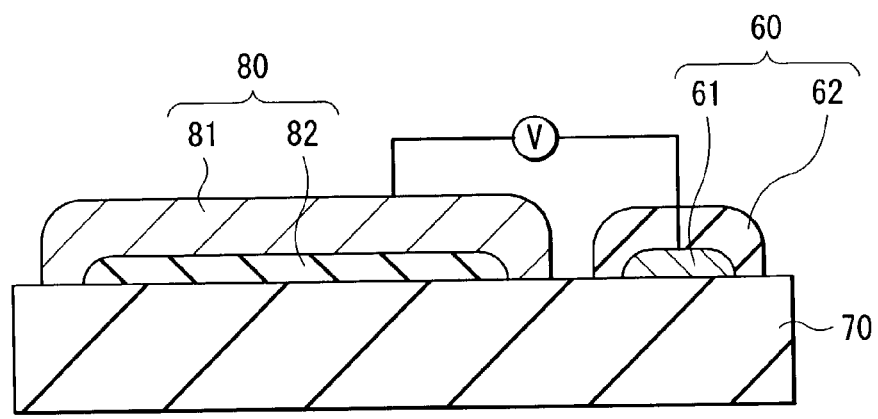
FIG. 3 is a sectional view showing a configuration of a carbon dioxide sensor according to a third embodiment of the invention.

FIG. 3 shows the configuration of a carbon dioxide sensor according to a third embodiment of the invention. The carbon dioxide sensor has the same configuration as that of the second embodiment except that a detection electrode 80 has the layer structure as the first embodiment. Therefore, the same components are indicated by the same numerals and the detail explanation thereof will be omitted.

The detection electrode 80 comprises a metal oxide layer 81 including metal oxide, a metal carbonate layer 82 including plural components of metal carbonate. The metal carbonate layer 82 is provided between the metal oxide layer 80 and the electrolyte 70. With such a layer structure, the influence of humidity can be decreased and the carbon dioxide sensing property can be improved. Preferably, the thickness of the metal oxide layer 81 is 10 nm to 500 $\mu$m and the thickness of the metal carbonate layer 82 is 10 nm to 500 $\mu$m, for example, because higher effects can be achieved.

The metal oxide included in the metal oxide layer 81 and the plural components of the metal carbonate included in the metal carbonate layer 82 are the same as that of the second embodiment. The metal carbonate layer 82 may contain the metal hydrogen carbonate because the metal hydrogen carbonate may be generated during the measurement of carbon dioxide.

The metal oxide layer 81 and the metal carbonate layer 82 are formed similar to the first embodiment.

According to the embodiment, the metal carbonate layer 82 and the metal oxide layer 81 on the electrolyte 70 are comprised in this order, so the influence of humidity can be reduced and the carbon dioxide sensing property can be improved.

Specifically, when the metal carbonate layer 82 is formed at a temperature lower than the melting point of the used metal, the higher effects can be achieved.

Figure 4:
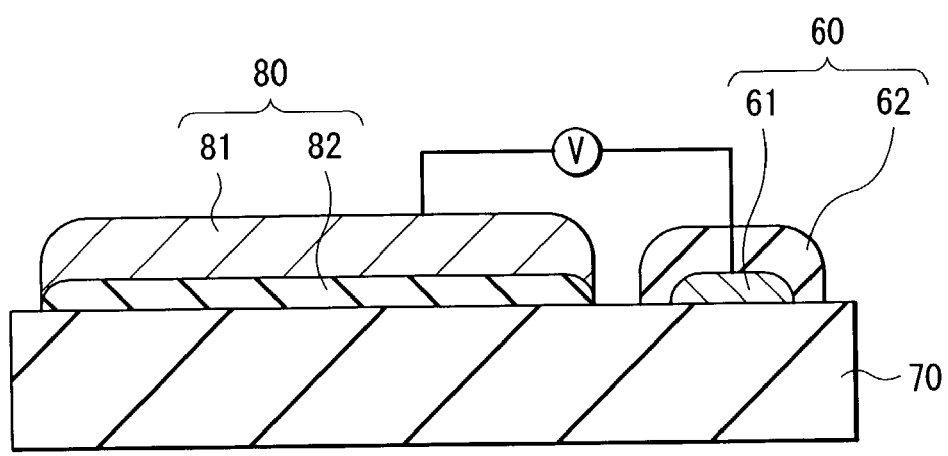
FIG. 4 is a sectional view showing a configuration of a carbon dioxide sensor according to a variation of the third embodiment of the invention.

In FIG. 3, the metal oxide layer 81 covers the top and side surfaces of the metal carbonate layer 82 completely and part of the metal oxide layer 81 contacts to the electrolyte 70. However, as shown in FIG. 4, the metal oxide layer 81 may cover at least part of the top surface of the metal carbonate layer 82 and be not in contact with the electrolyte 70.

EXAMPLE

Further, the specific examples of the invention will be described hereinbelow.

Example 1

A carbon dioxide sensor as shown in FIG. 1 was formed. First, NASICON powder was prepared by sol-gel method and a discoid electrolyte 30 having a diameter of 9 mm and a thickness of 1.2 mm was formed by using the NASICON powder. Next, a gold paste was applied to the entire surface of the electrolyte 30 together with a gold mesh 22 and a gold wire to be a lead 23, and a powder electrode 21 was formed by heat treatment at 800° C. for two hours in the atmosphere to form a counter electrode 20. Subsequently, a quartz glass tube 40 of 9 mm in diameter was attached to the electrolyte 30 on the side where the counter electrode 20 was provided with an adhesive layer 41 using an inorganic adhesive.

After that, lithium carbonate powder and an organic solvent containing 5% by mass of ethyl cellulose and 95% by mass of $\alpha$-terpineol were mixed with substantially equal weight each to form the paste, and the paste was applied to the surface of the electrolyte 30.

Indium chloride ($InCl_3$) powder and tin chloride ($SnCl_4$) powder were mixed by using water and heated at 1200° C. for two hours. The composite oxide powder of indium and tin with a grain size of about 0.5 $\mu$m to 1 $\mu$m was obtained. Then, the composite oxide powder and the organic solvent containing 5% by mass of ethyl cellulose and 95% by mass of $\alpha$-terpineol were mixed with substantially equal weight each to form the paste, and the paste was applied on the lithium carbonate paste layer.

Subsequently, heat-treatment was performed at 500° C. which was lower than the melting point of lithium carbonate in the atmosphere for 30 minutes to form a detection electrode 10 laminated a metal carbonate layer 12 having a thickness of about 20 $\mu$m and a metal oxide layer 11 having a thickness of about 20 $\mu$m. Thereby, the carbon dioxide sensor shown in FIG. 1 was obtained.

A carbon dioxide sensor as Comparative Example 1 to Example 1 was prepared like Example 1 except that lithium carbonate powder and the composite oxide powder of indium and tin were mixed with the organic solvent having substantially the equal weight with these powders to form the paste and the paste was applied to the surface of the electrolyte 30, and then the heat treatment was performed at 500° C. for 30 minutes in the atmosphere to form the detection electrode with about 40 $\mu$m in thickness.

Figure 5:
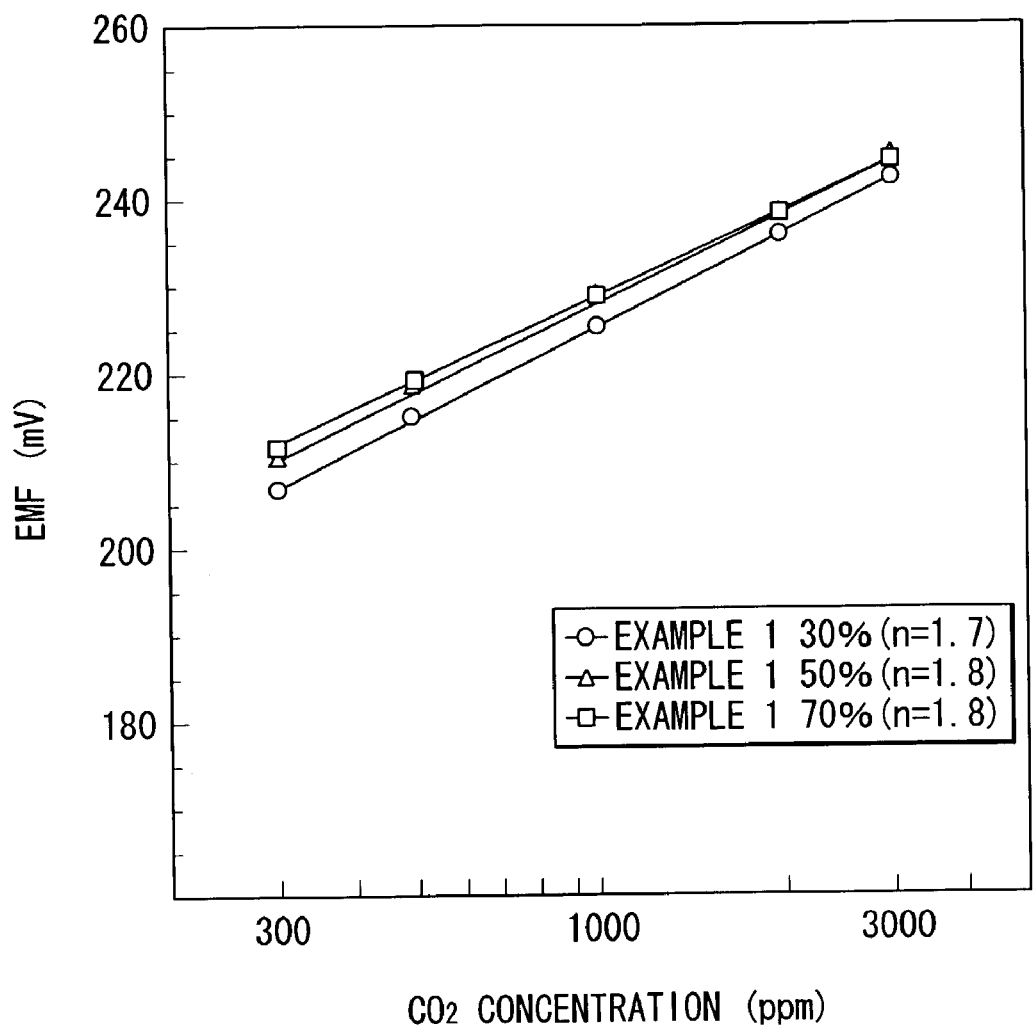
FIG. 5 is a characteristic view showing the relation of the carbon dioxide concentration and electromotive force by humidity according to Example 1 of the invention.
Figure 6:
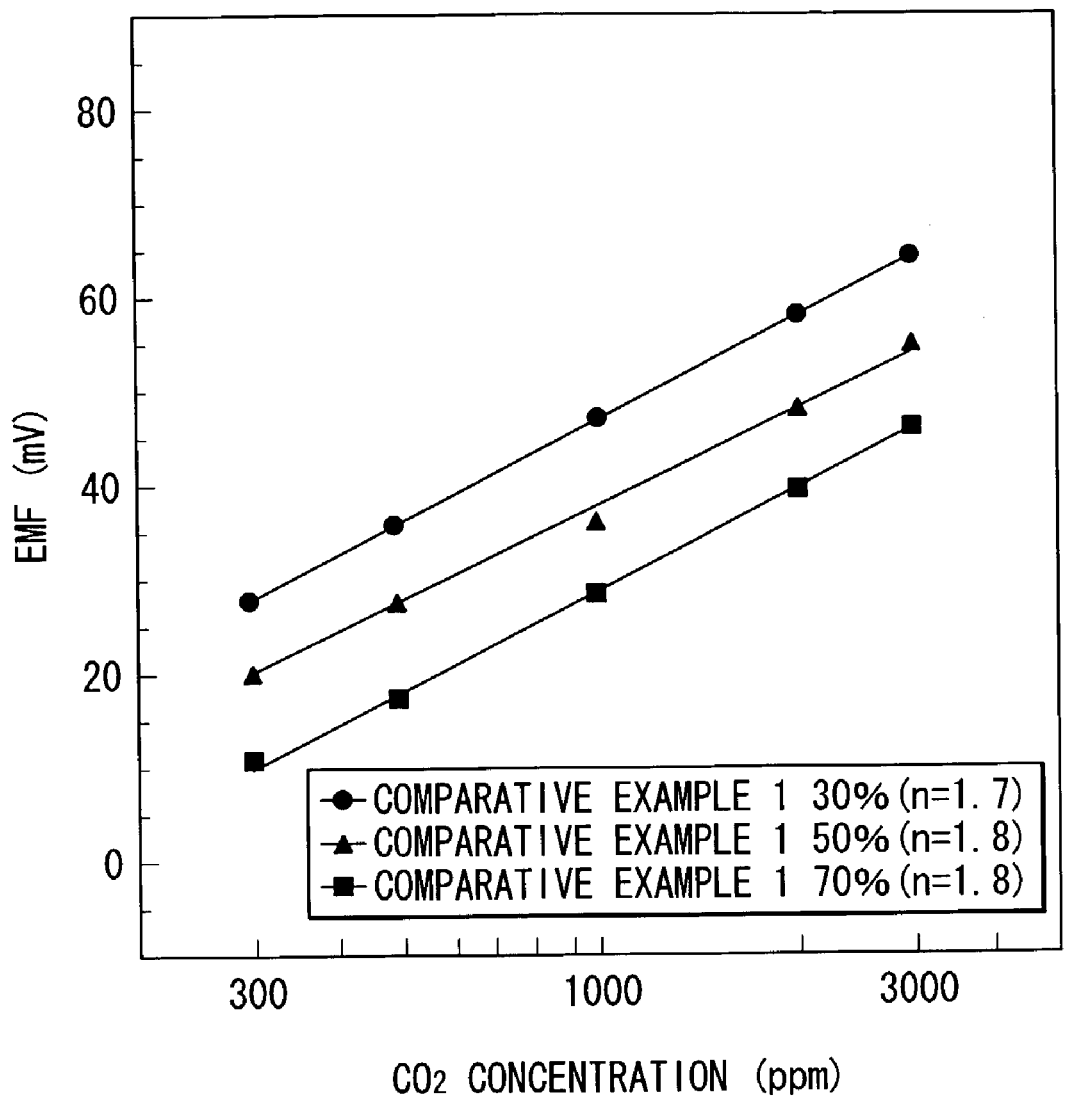
FIG. 6 is a characteristic view showing the relation of the carbon dioxide concentration and electromotive force by humidity according to Comparative Example 1 to Example 1 of the invention.

The relation of electromotive force and carbon dioxide concentration at room temperature at 30%, 50% and 70% humidity for the obtained carbon dioxide sensors of Example 1 and Comparative Example 1 were examined. The results of Example 1 and Comparative Example 1 are shown in FIG. 5 and FIG. 6, respectively. The value n is calculated from the gradient showing the relation between the carbon dioxide concentration and the absolute value of electromotive force and means the number of reaction electron regarding electrochemical reduction per carbon dioxide molecule. As shown in FIGS. 5 and 6, the difference of the absolute value of electromotive force to the carbon dioxide concentration by humidity is reduced and the influence on the sensitivity is also reduced. Namely, when the metal carbonate layer 12 and the metal oxide layer 11 are laminated in order from the electrolyte 30 side, we have found that the carbon dioxide is operatable at room temperature and has less influence of humidity, and the carbon dioxide sensing property can be improved.

As seen in the comparison of FIGS. 5 and 6, the absolute value of electromotive force to the carbon dioxide concentration of Example 1 was larger than that of Comparative Example 1. As a result, we have found that the laminate structure having the metal oxide layer 11 and the metal carbonate layer 12 improves the carbon dioxide sensing property.

Example 2

A carbon dioxide sensor was formed like Example 1 except that lithium carbonate paste was applied to the electrolyte 30, heated at 750° C., which was higher than the melting point of lithium carbonate, in the atmosphere, extracted at the time of melting and fusion bonding the metal carbonate layer 12, and after that the composite oxide paste of indium and tin was applied thereon and heated at 500° C. for 30 minutes in the atmosphere to form the metal oxide layer 11.

Figure 7:
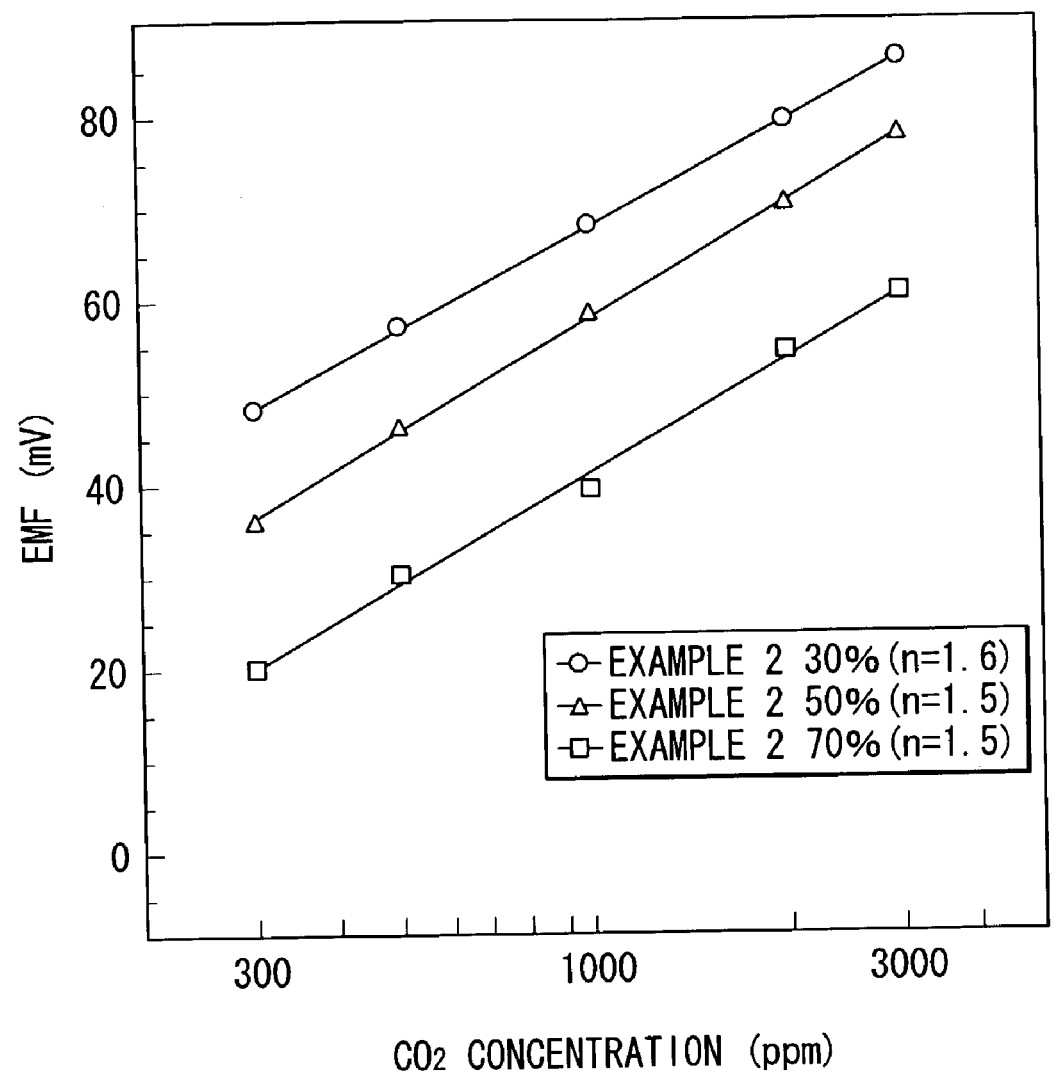
FIG. 7 is a characteristic view showing the relation of the carbon dioxide concentration and electromotive force by humidity according to Example 2 of the invention.

The relation of electromotive force and carbon dioxide concentration at room temperature at 30%, 50% and 70% humidity for the obtained carbon dioxide sensor of Example 2 were examined like the first embodiment. The results of Example 2 are shown in FIG. 7. As seen in the comparison of FIGS. 5 and 7, the difference of the absolute value of electromotive force to the carbon dioxide concentration by humidity of Example 1 was smaller than that of Example 2. That is, when the metal carbonate layer 12 is formed at a temperature lower than the melting point of the metal carbonate, we have found that the carbon dioxide sensor is operatable at room temperature and has less influence of humidity, and the carbon dioxide sensing property can be improved.

A carbon dioxide sensor as Comparative Example to Example 2, that is, lithium carbonate powder and the composite oxide powder of indium and tin were mixed and fusion bonded at a temperature higher than the melting point of lithium carbonate to form the detection electrode is not mentioned. However, because of the reaction of lithium carbonate with the composite oxide or the electrolyte, it is supposed. that the properties deserving evaluation cannot be obtained.

Examples 3-1 to 3-4

The carbon dioxide sensors shown in FIG. 1 were formed like Example 1 except for the change of the configuration of the detection electrode 10. Specifically, the complex carbonate paste of alkali metal carbonate of a first component and barium carbonate of a second component or alkali metal carbonate paste was applied to the electrolyte 30 and then dissolved at a temperature higher than the melting point of alkali metal carbonate in the atmosphere to fusion bond the metal carbonate layer 12, and the composite oxide paste of indium and tin was applied thereon and heated at 500° C., which is lower than the melting point of alkali metal carbonate in the atmosphere for 30 minutes to form the metal oxide layer 11.

At this time, the complex carbonate of potassium carbonate and barium carbonate was used in Example 3-1, potassium carbonate was used in Example 3-2, the complex carbonate of lithium carbonate and barium carbonate was used in Example 3-3, and lithium carbonate was used in Example 3-4. Example 3-4 is the same as Example 2. The complex carbonate was prepared by mixing alkali metal carbonate powder of the first component and barium carbonate powder of the second component at alkali metal carbonate:barium carbonate=1:2 in molar ratio and melting the mixed powder at a temperature higher than the melting point of alkali metal carbonate.

The relation of electromotive force and carbon dioxide concentration at room temperature at 30%, 50% and 70% humidity for the obtained carbon dioxide sensors of Example 3-1 to 3-4 were examined and the sensitivity and variation of electromotive force at carbon dioxide concentration of 350 ppm at 30% and 70% humidity were determined. The results are shown in Table 1. The sensitivity indicates the number of reaction electron n as explained in Example 1.

TABLE 1

| | Metal carbonate (Fusion bonding layer) | Sensitivity (Number of reaction electron n) | | | Variation of electromotive force at 350 ppm $CO_2$ |
|---|---|---|---|---|---|
| | | 30 % RH | 50% RH | 70% RH | (30%→70% RH) |
| Example 3-1 | $K_2CO_3 \cdot BaCo_3$ | 2.3 | 2.3 | 2.3 | 19 mV |
| Example 3-2 | $K_2CO_3$ | 2.4 | 2.5 | 2.6 | 21 mV |
| Example 3-3 | $Li_2CO_3 \cdot BaCO_3$ | 1.5 | 1.6 | 1.6 | 20 mV |
| Example 3-4 | $Li_2CO_3$ | 1.6 | 1.5 | 1.5 | 27 mV |

As shown in Table 1, according to Examples 3-1 and 3-3 including potassium carbonate or lithium carbonate and barium carbonate, compared to Examples 3-2 and 3-4 including only potassium carbonate or lithium carbonate, the variation of electromotive force by humidity was small. Namely, when the carbon dioxide sensor comprises the metal oxide layer 11 and the metal carbonate layer 12 including the plural components, we have found that it is operatable at room temperature and has less influence of humidity.

Examples 4-1 to 4-6

The carbon dioxide sensors were formed like the Examples 3-1 to 3-4 except that after applying the complex carbonate paste of alkali metal carbonate and barium carbonate or alkali metal carbonate paste to the electrolyte 30, the composite oxide paste of indium and tin were applied thereon and heated at 500° C. for 30 minutes to form the metal oxide layer 11 and metal carbonate layer 12. At this time, the complex carbonate of sodium carbonate and barium carbonate was used in Example 4-1, sodium carbonate was used in Example 4-2, the complex carbonate of potassium carbonate and barium carbonate was used in Example 4-3, potassium carbonate was used in Example 4-4, the complex carbonate of lithium carbonate and barium carbonate was used in Example 4-5 and lithium carbonate was used in Example 4-6.

The relation of electromotive force and carbon dioxide concentration at room temperature at 30%, 50% and 70% humidity for the carbon dioxide sensors of Examples 4-1 to 4-6 were examined like Examples 3-1 to 3-4. The results are shown in Table 2.

Additionally, from the results of Table 2, in Example 4-5 using lithium carbonate as the first component, the variation of electromotive force could be as low as 1 mV. That is, when including lithium carbonate, the influence of humidity can be reduced.

Examples 5-1 to 5-6, 6-1 to 6-6

The carbon dioxide sensors shown in FIG. 3 were formed by fusion bonding the metal carbonate layer 82 of complex carbonate of alkali metal carbonate and barium carbonate or of alkali metal carbonate like Examples 3-1 to 3-4 as Examples 5-1 to 5-6. At this time, the complex carbonate of sodium carbonate and barium carbonate was used in Example 5-1, sodium carbonate was used in Example 5-2, the complex carbonate of potassium carbonate and barium carbonate was used in Example 5-3, potassium carbonate was used in Example 5-4, the complex carbonate of lithium carbonate and barium carbonate was used in Example 5-5 and lithium carbonate was used in Example 5-6.

The carbon dioxide sensors shown in FIG. 3 were formed by forming the metal carbonate layer 82 of complex carbonate of alkali metal carbonate and barium carbonate or of alkali metal carbonate at a temperature lower than the melting point of alkali metal carbonate like Examples 4-1 to 4-6 as Examples 6-1 to 6-6. At this time, the complex carbonate of sodium carbonate and barium carbonate was used in Example 6-1, sodium carbonate was used in Example 6-2, the complex carbonate of potassium carbonate and barium carbonate was used in Example 6-3, potassium carbonate was used in Example 6-4, the complex carbonate

TABLE 2

|  | Metal carbonate (Non-fusion bonding layer) | Sensitivity (Number of reaction electron n) | | | Variation of electromotive force at 350 ppm $CO_2$ |
| --- | --- | --- | --- | --- | --- |
|  |  | 30% RH | 50% RH | 70% RH | (30%→70% RH) |
| Example 4-1 | $Na_2CO_3 \cdot BaCO_3$ | 1.7 | 1.6 | 1.6 | 12 mV |
| Example 4-2 | $Na_2CO_3$ | 1.6 | 1.6 | 1.7 | 21 mV |
| Example 4-3 | $K_2CO_3 \cdot BaCO_3$ | 2.2 | 2.2 | 2.2 | 17 mV |
| Example 4-4 | $K_2CO_3$ | 2.1 | 2.1 | 2.2 | 25 mV |
| Example 4-5 | $Li_2CO_3 \cdot BaCO_3$ | 1.7 | 1.7 | 1.7 | 1 mV |
| Example 4-6 | $Li_2CO_3$ | 1.7 | 1.8 | 1.8 | 7 mV |

As shown in Table 2, similar to Examples 3-1 and 3-3, Examples 4-1, 4-3, 4-5 including alkali metal carbonate and barium carbonate have smaller variation of electromotive force by humidity. Namely, when the carbon dioxide sensor comprises the metal carbonate layer 12 including the plural components, we have found that it is operatable at room temperature and has less influence of humidity.

Comparing Table 1 with Table 2, the variation of electromotive force by humidity of Examples 4-3 and 4-5 was smaller than that of Examples 3-1 and 3-3. As a result, we have found that forming the metal carbonate layer 12 at a temperature lower than the melting point of used metal carbonate can reduce the influence of humidity.

of lithium carbonate and barium carbonate was used in Example 6-5 and lithium carbonate was used in Example 6-6.

The relation of electromotive force and carbon dioxide concentration at room temperature at 30%, 50% and 70% humidity for the carbon dioxide sensors of Examples 5-1 to 5-6 and 6-1 to 6-6 were examined like Examples 3-1 to 3-4.

The long-term stability test at high temperature ant humidity was conducted for the carbon dioxide sensors of Examples 6-1 to 6-6. Specifically, the electromotive force was measured at room temperature at the carbon dioxide concentration of 350 ppm and at 30% humidity, and it was kept in a constant temperature bath of 60° C. and 80% humidity for 500 hours. After that, the electromotive force was again measured at room temperature at the carbon dioxide concentration of 350 ppm and at 30% humidity and the variation of electromotive force was determined. These results are shown in Table 3 and Table 4.

TABLE 3

| Metal carbonate (Non-fusion bonding layer) | Sensitivity (Number of reaction electron n) | | | Variation of electromotive force at 350 ppm $CO_2$ |
|---|---|---|---|---|
| | 30% RH | 50% RH | 70% RH | (30%→70% RH) |
| Example 5-1 $Na_2CO_3 \cdot BaCO_3$ | 2.1 | 2.0 | 2.1 | 12 mV |
| Example 5-2 $Na_2CO_3$ | 1.8 | 1.9 | 1.9 | 13 mV |
| Example 5-3 $K_2CO_3 \cdot BaCO_3$ | 2.2 | 2.3 | 2.3 | 18 mV |
| Example 5-4 $K_2CO_3$ | 2.4 | 2.5 | 2.5 | 20 mV |
| Example 5-5 $Li_2CO_3 \cdot BaCO_3$ | 1.6 | 1.6 | 1.7 | 19 mV |
| Example 5-6 $Li_2CO_3$ | 1.6 | 1.6 | 1.5 | 29 mV |

TABLE 4

| Metal carbonate (Non-fusion bonding layer) | Sensitivity (Number of reaction electron n) | | | Variation of electromotive force at 350 ppm $CO_2$ (mV) | |
|---|---|---|---|---|---|
| | | | | Humidity | After stored at high temperature and humidity |
| | 30% RH | 50% RH | 70% RH | 30%→70% | 30% RH |
| Example 6-1 $Na_2CO_3 \cdot BaCO_3$ | 1.7 | 1.6 | 1.6 | 12 | 70 |
| Example 6-2 $Na_2CO_3$ | 1.6 | 1.6 | 1.7 | 21 | 100 |
| Example 6-3 $K_2CO_3 \cdot BaCO_3$ | 2.2 | 2.2 | 2.2 | 17 | 80 |
| Example 6-4 $K_2CO_3$ | 2.1 | 2.1 | 2.2 | 25 | 150 |
| Example 6-5 $Li_2CO_3 \cdot BaCO_3$ | 1.7 | 1.7 | 1.7 | 1 | 20 |
| Example 6-6 $Li_2CO_3$ | 1.7 | 1.8 | 1.8 | 7 | 90 |

As shown in Tables 3 and 4, similar to Examples 3-1 to 3-4 and 4-1 to 4-6, Examples 5-1, 5-3, 5-5, 6-1, 6-3, and 6-5 including alkali metal carbonate and barium carbonate have smaller variation of electromotive force by humidity. In addition, as shown in Table 4, Examples 6-1, 6-3 and 6-5 including alkali metal carbonate and barium carbonate have smaller variation of electromotive force after stored at high temperature and humidity.

Comparing Table 3 with Table 4, the variation of electromotive force by humidity of Examples 6-3 and 6-5 is smaller than that of Examples 5-3 and 5-5. Table 4 also reveals that Example 6-5 using lithium carbonate as the first component can have very small variation of electromotive force as small as 1 mV.

More specifically, the carbon dioxide sensor shown in FIG. 3, which has the detection electrode 80 and the counter electrode 60 on the same side of the electrolyte 70, is operatable at room temperature and reduce the influence of humidity when comprising the metal oxide layer 81 and the metal carbonate layer 82 including the plural components, like the carbon dioxide sensor in which the detection electrode 80 is provided on the opposite side of the counter electrode 60. It is more preferable to form the carbon dioxide sensor at a temperature lower than the melting point of metal carbonate contained in the metal carbonate layer 82 and to include lithium carbonate in the first component.

Incidentally, a carbon oxide sensor shown in FIG. 4 was formed and examined the properties like Examples 5-1 to 5-6 and 6-1 to 6-6, and it was confirmed that the same results were achieved.

Examples 7-1 and 7-2

The carbon oxide sensors were formed like Example 6-3 except that calcium carbonate was used instead of barium carbonate in Example 7-1 and strontium carbonate was used instead of barium carbonate in Example 7-2 as the second component. The complex carbonate of lithium carbonate and calcium carbonate was used in Example 7-1 and the complex carbonate of lithium carbonate and strontium carbonate was used in Example 7-2, and a metal carbonate layer 42 was formed at a temperature lower than the melting point of the metal carbonate. The relation of electromotive force and carbon dioxide concentration at room temperature at 30%, 50% and 70% humidity for the carbon dioxide sensors of Examples 7-1 and 7-2 was examined and the long-term stability test at high temperature ant humidity was conducted, similar to Example 6-5. These results are shown in Table 5 together with the results of Examples 6-5 and 6-6.

TABLE 5

| | Metal carbonate (Non-fusion bonding layer) | Sensitivity (Number of reaction electron n) | | | Variation of electromotive force at 350 ppm $CO_2$ (mV) | |
|---|---|---|---|---|---|---|
| | | | | | Humidity | After stored at high temperature and humidity |
| | | 30% RH | 50% RH | 70% RH | 30%→70% | 30% RH |
| Example 6-5 | $Li_2CO_3 \cdot BaCO_3$ | 1.7 | 1.7 | 1.7 | 1 | 20 |
| Example 7-1 | $Li_2CO_3 \cdot CaCO_3$ | 1.9 | 1.9 | 2.0 | 4 | 40 |
| Example 7-2 | $Li_2CO_3 \cdot SRCO_3$ | 1.9 | 1.8 | 1.8 | 6 | 50 |
| Example 6-6 | $Li_2CO_3$ | 1.7 | 1.8 | 1.8 | 7 | 90 |

As shown in Table 5, like Example 6-5, Example 7-1 using calcium carbonate instead of barium carbonate and Example 7-2 using strontium carbonate instead of barium carbonate could reduce the variation of electromotive force by humidity and after storage at high temperature and humidity, compared to Example 6-6 using only lithium carbonate. That is, when using other alkali earth metal carbonate as the second component, we have found that it is operatable at room temperature and has less influence of humidity.

Examples 8-1 to 8-8

The carbon dioxide sensors were formed like Example 6-1 except that the second component was varied as shown in Table 6. That is, the complex carbonate of sodium carbonate and copper carbonate was used in Example 8-1, the complex carbonate of sodium carbonate and nickel carbonate was used in Example 8-2, the complex carbonate of sodium carbonate and manganese carbonate was used in Example 8-3, the complex carbonate of sodium carbonate and lead carbonate was used in Example 8-4, the complex carbonate of sodium carbonate and zinc carbonate was used in Example 8-5, the complex carbonate of sodium carbonate and indium carbonate was used in Example 8-6, the complex carbonate of sodium carbonate and bismuth carbonate was used in Example 8-7 and the complex carbonate of sodium carbonate and cadmium carbonate was used in Example 8-8, and the metal carbonate layer 82 was formed at a temperature lower than the melting point of the metal carbonate.

TABLE 6

| | Metal carbonate (Non-fusion bonding layer) | Sensitivity (Number of reaction electron n) | | | Variation of electromotive force at 350 ppm $CO_2$ (mV) | |
|---|---|---|---|---|---|---|
| | | | | | Humidity | After stored at high temperature and humidity |
| | | 30% RH | 50% RH | 70% RH | 30%→70% | 30% RH |
| Example 6-1 | $Na_2CO_3 \cdot BaCO_3$ | 1.7 | 1.6 | 1.6 | 12 | 70 |
| Example 8-1 | $Na_2CO_3 \cdot CuCO_3$ | 2.4 | 2.3 | 2.5 | 16 | 70 |
| Example 8-2 | $Na_2CO_3 \cdot NiCO_3$ | 2.3 | 2.1 | 2.1 | 19 | 80 |
| Example 8-3 | $Na_2CO_3 \cdot MnCO_3$ | 2.1 | 2.1 | 2.2 | 14 | 60 |
| Example 8-4 | $Na_2CO_3 \cdot PbCO_3$ | 2.4 | 2.3 | 2.3 | 10 | 70 |
| Example 8-5 | $Na_2CO_3 \cdot ZnCO_3$ | 2.1 | 2.0 | 2.0 | 12 | 80 |
| Example 8-6 | $Na_2CO_3 \cdot In_2(CO)_3$ | 2.3 | 2.2 | 2.2 | 15 | 70 |
| Example 8-7 | $Na_2CO_3 \cdot Bi_2(CO)_3$ | 2.4 | 2.3 | 2.1 | 18 | 80 |
| Example 8-8 | $Na_2CO_3 \cdot CdCO_3$ | 2.5 | 2.4 | 2.4 | 13 | 90 |
| Example 6-2 | $Na_2CO_3$ | 1.6 | 1.6 | 1.7 | 21 | 100 |

The relation of electromotive force and carbon dioxide concentration at room temperature at 30%, 50% and 70% humidity for the carbon dioxide sensors of Examples 8-1 to 8-8 was examined and the long-term stability test at high temperature ant humidity was conducted, similar to Example 6-1. These results are shown in Table 6 together with the results of Examples 6-1 and 6-2.

As shown in Table 6, like Example 6-1, Example 8-1 to 8-8 using transition metal carbonate, lead carbonate, zinc carbonate, indium carbonate, bismuth carbonate or cadmium carbonate instead of barium could reduce the variation of electromotive force by humidity and after storage at high temperature and humidity, compared to Example 6-2 using only sodium carbonate. That is, when using the transition metal carbonate, lead carbonate, zinc carbonate, indium carbonate, bismuth carbonate or cadmium carbonate as the second component, we have found that it is operatable at room temperature and has less influence of humidity.

Examples 9-1 and 9-2

The carbon dioxide sensors were formed like Example 6-1 except that rubidium carbonate was used instead of sodium carbonate in Example 9-1 and cesium carbonate was used instead of sodium carbonate in Example 9-2 as the first component. That is, the complex carbonate of rubidium carbonate and barium carbonate was used in Example 9-1 and the complex carbonate of cesium carbonate and barium carbonate was used in Example 9-2, and the metal carbonate layer 42 was formed at a temperature lower than the melting point of the metal carbonate. The relation of electromotive force and carbon dioxide concentration at room temperature at 30%, 50% and 70% humidity for the carbon dioxide sensors of Examples 9-1 and 9-2 was examined and the long-term stability test at high temperature and humidity was conducted, similar to Example 6-1. The results are shown in Table 7.

TABLE 7

|  | Metal carbonate (Non-fusion bonding layer) | Sensitivity (Number of reaction electron n) | | | Variation of electromotive force at 350 ppm $CO_2$ (mV) | |
|---|---|---|---|---|---|---|
|  |  | 30% RH | 50% RH | 70% RH | Humidity 30%→70% | After stored at high temperature and humidity 30% RH |
| Example 9-1 | $Rb_2CO_3 \cdot BaCO_3$ | 1.4 | 1.5 | 1.6 | 25 | 80 |
| Example 9-2 | $Cs_2CO_3 \cdot BaCO_3$ | 1.5 | 1.6 | 1.5 | 23 | 70 |

As shown in Table 7, Examples 9-1 and 9-2 using rubidium carbonate or cesium carbonate as the first component could reduce the influence of humidity at the same level as Example 6-2 using only sodium carbonate. Although it is not shown in Table 7, it can be considered that since rubidium carbonate and cesium carbonate have deliquescence, they are affected by humidity when using alone and the sufficient properties cannot be achieved. That is, when the carbon dioxide sensor comprises the second component when using other alkali metal carbonate as the first component, we have found that it is operatable at room temperature and has less influence of humidity.

Example 10-1

A carbon dioxide sensor shown in FIG. 2 was formed like Example 3-2 except that the complex carbonate of lithium carbonate and barium carbonate, and the composite oxide of indium and tin was mixed at 1:1 in mass ratio to prepare paste and applied to the electrolyte 70 and heated at 500° C. for 30 minutes to form the detection electrode 50. Another carbon dioxide sensor was also formed like Example 10-1 except that lithium carbonate and the composite oxide of indium and tin was mixed at 1:1 in mass ratio to form the detection electrode as Comparative Example 10-1. Comparative Example 10-1 is the same as Comparative Example 1.

The relation of electromotive force and carbon dioxide concentration at room temperature at 30%, 50% and 70% humidity for the carbon dioxide sensors of Example 10-1 and Comparative Example 10-1 was examined like Example 3-2, and the long-term stability test at high temperature ant humidity was conducted, similar to Example 6-3. The results are shown in Table 8.

TABLE 8

| | Metal carbonate (Non-fusion bonding layer) | Sensitivity (Number of reaction electron n) | | | Variation of electromotive force at 350 ppm $CO_2$ (mV) | |
|---|---|---|---|---|---|---|
| | | | | | Humidity | After stored at high temperature and humidity |
| | | 30% RH | 50% RH | 70% RH | 30%→70% | 30% RH |
| Example 10-1 | $Li_2CO_3 \cdot BaCO_3$ | 1.9 | 2.0 | 2.0 | 5 | 30 |
| Example 10-2 | $Li_2CO_3$ | 1.7 | 1.8 | 1.8 | 18 | 100 |

As shown in Table 8, Example 10-1 diffusing the complex carbonate of lithium carbonate and barium carbonate could reduce the variation of electromotive force by humidity and after stored at high temperature and humidity like Examples 3-2, 4-3, 5-3 and 6-3, compared to Comparative Example 10-1 using lithium carbonate alone. That is, it is fount that the carbon dioxide sensor forming the detection electrode 50 by diffusing metal carbonate and metal oxide as shown in FIG. 2 is operatable at room temperature and has less influence of humidity if metal carbonate including the plural components was contained.

Although the invention has been described by the foregoing embodiments and examples, the invention is not limited to the embodiments and the examples but can be variously modified. For example, in the first embodiment and examples, the detection electrodes 10 and 80 comprise the metal oxide layers 11 and 81 and the metal carbonate layers 12 and 82, or the detection electrode 50 is formed by the layer including metal oxide and metal carbonate of the plural components. However, it may further include other components. The metal oxide layers 11 and 81 may contain other substances in addition to the above-described metal oxides and the metal carbonate layers 12 and 82 may contain other substances other than the above-described metal carbonates and metal hydrogen carbonates. Further, the detection electrodes 50 and 80 may contain other substances other than the above-described metal oxides, metal carbonates and metal hydrogen carbonate.

As described above, according to the first carbon dioxide sensor of the invention, the metal oxide layer and the metal carbonate layer placed between the metal oxide layer and the electrolyte are included. As a result, it is operative at room temperature and has less influence of humidity, and furthermore, the carbon dioxide sensing property can be improved. Therefore, the carbon dioxide concentration can be easily detected with high accuracy.

Specifically, according to the carbon dioxide sensor in which the metal carbonate layer contains lithium carbonate and the carbon dioxide sensor in which the metal carbonate layer is formed at a temperature lower than the melting point of containing metal carbonate, the influence of humidity can be reduced and the carbon dioxide sensing property can be improved.

According to the second carbon dioxide sensor of the invention, the detection electrode comprises the metal oxide and the metal carbonate including plural components. As a result, it is operative at room temperature and has less influence of humidity and therefore, the carbon dioxide concentration can be easily detected with high accuracy.

Specifically, according to the carbon dioxide sensor in which the detection electrode include the fist component of alkali metal carbonate and the second component of at least one element selected from the group consisting of alkali earth metal carbonate, transition metal carbonate, zinc carbonate, cadmium carbonate, indium carbonate, lead carbonate and bismuth carbonate, and further the first component includes lithium carbonate and the second component includes at least one element selected from the group consisting of barium carbonate, potassium carbonate and strontium carbonate, the influence of humidity can be reduced.

Further, according to the carbon dioxide sensor in which the detection electrode comprises the metal oxide layer and the metal carbonate layer placed between the metal oxide layer and the electrolyte, the influence of humidity can be reduced and the carbon dioxide sensing property can be improved.

Furthermore, according to the carbon dioxide sensor in which the metal carbonate layer is formed at a temperature lower than a melting point of containing metal carbonate, the higher effects can be achieved.

What is claimed is:

1. A carbon dioxide sensor provided with a detection electrode and a counter electrode on an electrolyte, wherein the detection electrode comprises a metal oxide layer including a metal oxide, and a metal carbonate layer including a metal carbonate and placed between the metal oxide layer and the electrolyte,
    wherein the metal oxide includes at least one element selected from the group consisting of tin oxide, indium oxide, cobalt oxide, tungsten oxide, zinc oxide, lead oxide, copper oxide, iron oxide, nickel oxide, chromium oxide, cadmium oxide and bismuth oxide, and
    wherein the metal carbonate includes a first component of alkali metal carbonate and a second component of at least one element selected from the group consisting of alkali earth metal carbonate, carbonate of an element selected from Group 4 to Group 11 in long-form periodic table, zinc carbonate, cadmium carbonate, indium carbonate, lead carbonate and bismuth carbonate.

2. A carbon dioxide sensor according to claim 1, wherein the metal carbonate layer is formed at a temperature lower than a melting point of containing metal carbonate.

3. A carbon dioxide sensor provided with a detection electrode and a counter electrode on an electrolyte, wherein the detection electrode comprises a metal oxide layer, including a metal oxide, and a metal carbonate layer including a metal carbonate and placed between the metal oxide layer and the electrolyte,
   wherein the metal oxide contains a composite oxide including tin and indium, and
   wherein the metal carbonate includes a first component of alkali metal carbonate and a second component of at least one element selected from the group consisting of alkali earth metal carbonate, carbonate of an element selected from Group 4 to Group 11 in long-form periodic table, zinc carbonate, cadmium carbonate, indium carbonate, lead carbonate and bismuth carbonate.

\* \* \* \* \*